US012735681B2

(12) United States Patent
Sarioglu et al.

(10) Patent No.: US 12,735,681 B2
(45) Date of Patent: Sep. 15, 2026

(54) FILTRATION-BASED SYSTEMS AND METHODS FOR ISOLATION OF CLUSTERED PARTICLES

(71) Applicant: Georgia Tech Research Corporation, Atlanta, GA (US)

(72) Inventors: Ali Fatih Sarioglu, Atlanta, GA (US); Mert Boya, Atlanta, GA (US)

(73) Assignee: Georgia Tech Research Corporation, Atlanta, GA (US)

(*) Notice: Subject to any disclaimer, the term of this patent is extended or adjusted under 35 U.S.C. 154(b) by 1307 days.

(21) Appl. No.: 17/619,276

(22) PCT Filed: Jun. 17, 2020

(86) PCT No.: PCT/US2020/038083
§ 371 (c)(1),
(2) Date: Dec. 15, 2021

(87) PCT Pub. No.: WO2020/257247
PCT Pub. Date: Dec. 24, 2020

(65) Prior Publication Data
US 2022/0298489 A1 Sep. 22, 2022

Related U.S. Application Data

(60) Provisional application No. 62/862,211, filed on Jun. 17, 2019.

(51) Int. Cl.
*C12N 5/09* (2010.01)
*B01L 3/00* (2006.01)
(Continued)

(52) U.S. Cl.
CPC ...... *C12N 5/0693* (2013.01); *B01L 3/502761* (2013.01); *C12M 23/12* (2013.01); *C12M 25/04* (2013.01); *B01L 2200/0647* (2013.01)

(58) Field of Classification Search
CPC ............ C12N 5/0693; B01L 3/502761; B01L 2200/0647; C12M 23/12; C12M 25/04; C12M 47/04
See application file for complete search history.

(56) References Cited

U.S. PATENT DOCUMENTS 5,994,133 A 11/1999 Mejs et al.
9,458,489 B2 10/2016 Lim et al.
(Continued)

FOREIGN PATENT DOCUMENTS

CN 1338970 A 3/2002
CN 102791616 A 11/2012
(Continued)

OTHER PUBLICATIONS

International Search Report and Written Opinion from Application No. PCT/US2020/038083 dated Oct. 4, 2020.
(Continued)

*Primary Examiner* — Tracy Vivlemore
*Assistant Examiner* — Thomas R. Amick
(74) *Attorney, Agent, or Firm* — TROUTMAN PEPPER LOCKE LLP; Ryan A. Schneider; Korbin M. Blunck

(57) ABSTRACT

An embodiment of the disclosed technology provides an isolation device for isolating clustered particles. The isolation device can include an inlet configured to receive a fluid and an outlet configured to output the fluid. The fluid can include a plurality of non-clustered particles and a plurality of clustered particles. The isolation device can include a plurality of microwells. Each microwell can have a plurality of sidewalls and a bottom surfacing having a meshed trapping region. The meshed trapping region can capture the plurality of clustered particles while allowing the non-clustered particles to pass. The outputted fluid can include
(Continued)

the plurality of non-clustered particle and be substantially free of the plurality of clustered particles.

41 Claims, 14 Drawing Sheets

(51) Int. Cl.

| | |
|---|---|
| ***C12M 1/12*** | (2006.01) |
| ***C12M 1/32*** | (2006.01) |

(56) References Cited

U.S. PATENT DOCUMENTS

| | | | |
|---|---|---|---|
| 2010/0098742 | A1 | 4/2010 | Vacanti et al. |
| 2010/0181288 | A1 | 7/2010 | Tang et al. |
| 2010/0247386 | A1 | 9/2010 | Deutsch et al. |
| 2014/0315295 | A1 | 10/2014 | Makarova et al. |
| 2014/0357511 | A1 | 12/2014 | Handique et al. |
| 2015/0368599 | A1 | 12/2015 | Maher et al. |
| 2016/0279637 | A1 | 9/2016 | Sarioglu et al. |
| 2016/0282338 | A1 | 9/2016 | Miklas et al. |
| 2017/0198248 | A1 | 7/2017 | Kinuta |
| 2018/0362917 | A1 | 12/2018 | Kondo et al. |

FOREIGN PATENT DOCUMENTS

| | | | |
|---|---|---|---|
| CN | 105745021 | A | 7/2016 |
| CN | 107109340 | A | 8/2017 |
| JP | 2013-521001 | A | 6/2016 |
| JP | 2016-539331 | A | 12/2016 |
| KR | 10-2012-0129679 | | 11/2012 |
| WO | 2016069917 | A1 | 5/2016 |
| WO | 2017/022810 | A1 | 2/2017 |

OTHER PUBLICATIONS https://en.wikipedia.org/w/index/php?title=Mesh&oldid=899352511 'Mesh' May 29, 2019.

Office Action from Japanese Application 2021-574907 dated Jun. 20, 2024.

Search Report from EP Application No. 20826411.9 dated May 25, 2023.

Office Action from Chinese Application No. 101080052163.8 dated Jul. 19, 2024.

Office Action from Chinese Application No. 202080052163.8 dated Apr. 1, 2024.

Office Action from Chinese Application No. 202080052163.8 dated May 6, 2025 (with English translation).

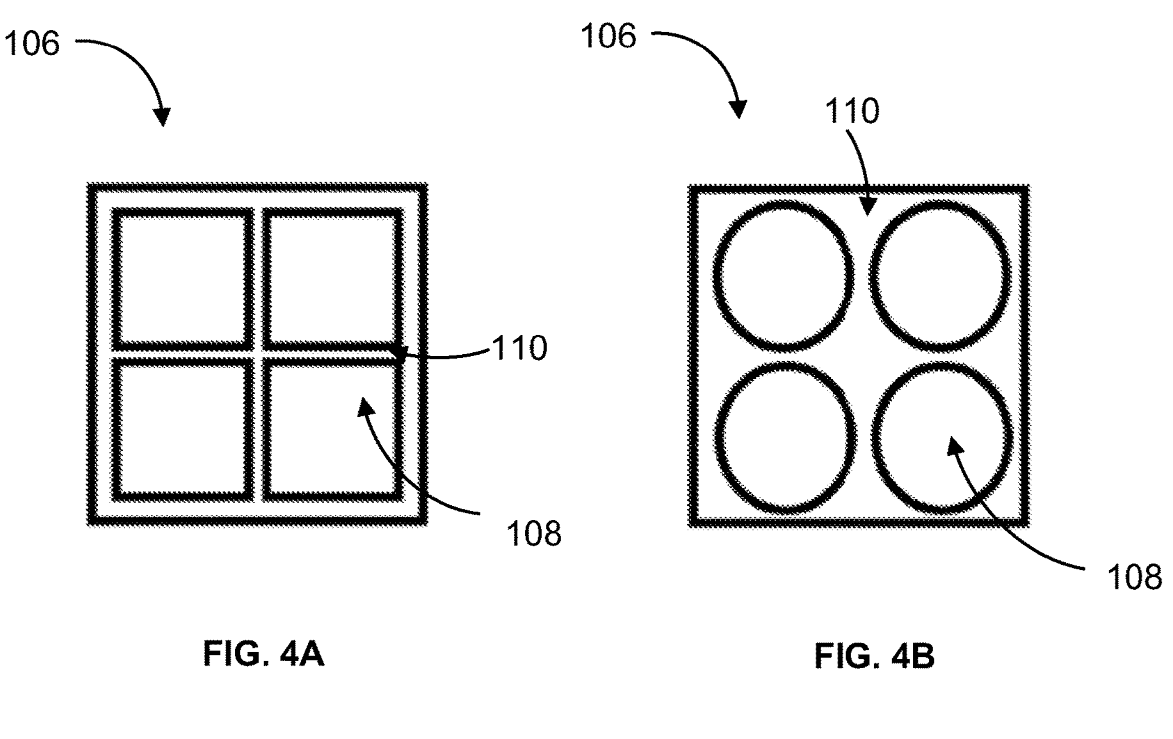
FIG. 4A
FIG. 4B
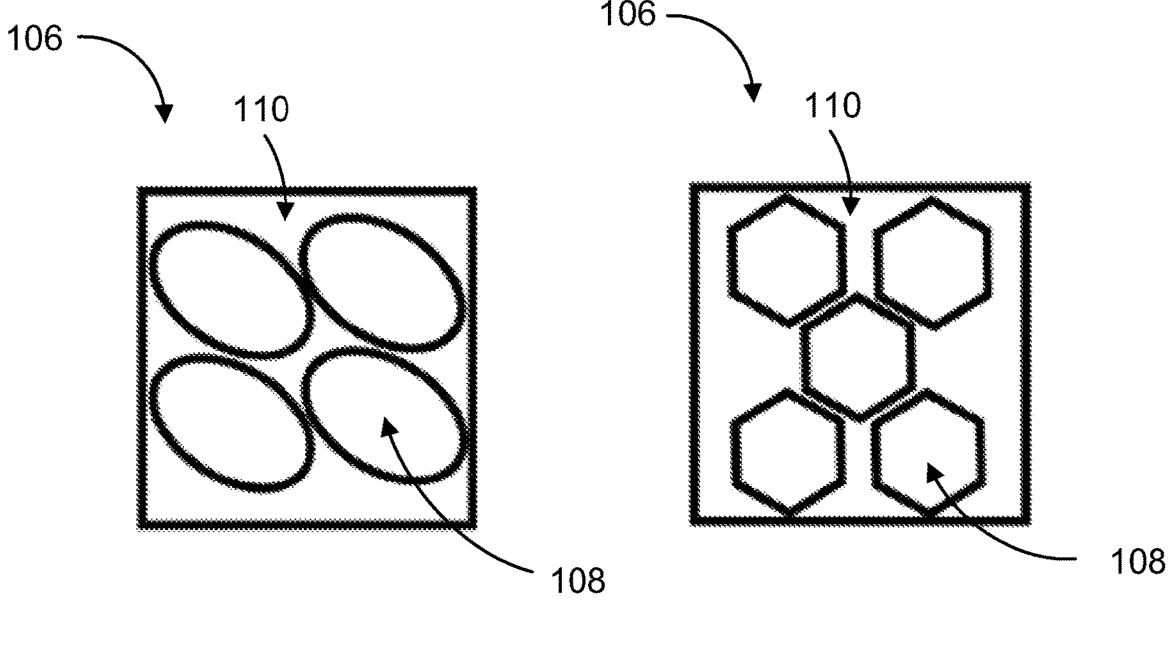
FIG. 4C
FIG. 4D 102
104a
110
108

106
104a
110
108

102
104a
110
108

106
110
104a
108

FILTRATION-BASED SYSTEMS AND METHODS FOR ISOLATION OF CLUSTERED PARTICLES

CROSS-REFERENCE TO RELATED APPLICATIONS

This application claims priority, and benefit under 35 U.S.C. § 119(e), to U.S. Provisional Patent Application No. 62/862,211 filed 17 Jun. 2019, which is hereby incorporated by reference in its entirety as if fully set forth below.

FIELD OF DISCLOSURE

The disclosed technology relates generally to systems and methods for isolating clustered particles in a fluid, and more particularly to systems and methods for isolating clustered particles in a fluid at a high volumetric flow rate without dissociation of the clustered particles.

BACKGROUND

Clustered particles, including circulating tumor cell clusters (CTC clusters) and other forms of cancerous cell clusters, enriched from the bloodstream of cancer patients can provide valuable information on the stage of a disease, enable minimally invasive prognosis and diagnosis, enhance the understanding of metastasis, and ultimately take part in the improvement of cancer treatment.

In particular, the metastatic propensity of CTC clusters can be up to 100 times higher than single CTCs. This high metastatic propensity can be linked to decreased apoptosis and prolonged survival attributes. Moreover, CTC-neutrophil clusters can have increased metastatic potential in advanced breast cancer patients, where the neutrophil-escorted CTC clusters demonstrate higher expression levels of proliferation marker protein (Ki67) and of genes associated with cell-cycle progression. Clinical studies have illustrated that the presence of CTC clusters can be associated with shorter progression free survival and overall survival in patients.

Even though clustered particles can be detected using existing isolation technologies designed to detect single cells, such as single CTCs, the existing isolation technologies can have a low sensitivity and specificity for capturing clustered particles. Although microfiltration techniques can be simple, this technique can be ill-suited for the enrichment of certain clustered particles. For example, CTC clusters can pass through small constrictions by reorganizing as single-file chain-like structures that reduce their hydrodynamic resistance, especially at higher pressures commonly used in traditional filtration-based systems. Moreover, in most cases, the high shear force experienced within filtration-based systems can dissociate the clustered particles into single cells, thereby precluding efficient enrichment. Additionally, antibody-based enrichment systems can be used for isolation of single cells and clustered particles. However, this technique can be difficult when attempting to isolate heterogenous CTC single cells and clusters due to their dependency on specific cell surface antigens. The smaller surface area-to-volume ratio of CTC clusters can negatively impact the capture efficiencies of these antibody-based technologies, rendering them inefficient platforms for CTC cluster enrichment.

Additionally, a two-stage continuous-flow microfluidic chip to isolate CTC clusters from whole blood by utilizing a modified version of deterministic lateral displacement (DLD) method has been developed. However, this technology can have a low throughput of less than 2.5 mL/hour. This low throughput can limit use in clinical applications, where large amounts of blood need to be processed due to extreme scarcity of clusters. Furthermore, this technology can fall short of isolating relatively smaller 2 or 3-cell clusters, which constitute the majority of CTC clusters observed in cancer patients. Non-equilibrium inertial separation array (NISA) can have a competitive flow rate of operation. However, due to the microfluidic channel size restriction, cell clusters composed of more than 5 to 6 cells can be prone to experience high shear stress, which can damage and dissociate these relatively bigger clusters. Lastly, significantly large clusters observed in patient samples can lead to clogging of microfluidic channels.

Accordingly, a need exists for systems and methods for isolating clustered particles at a high volumetric flow rate without resulting in dissociation of the clustered particles.

SUMMARY

The present disclosure relates to a device for isolating clustered particles from a sample of fluid. The isolation device can include a plurality of microwells having a bottom surface with a meshed trapping region. The meshed trapping region can be divided into a plurality of apertures using one or more barrier lines. When a sample of fluid including non-clustered particles and clustered particles is passed through the isolation device, the fluid can be funneled into the microwells. The apertures can be sized such that the non-clustered particles can pass through the apertures, while the clustered particles can be captured within the meshed trapping region. Once captured, the clustered particles can be retrieved from the meshed trapping region for molecular and functional analysis.

The disclosed technology can include a device for isolating clustered particles. The device can include an inlet configured to receive a fluid, a plurality of microwells, and an outlet configured to output the fluid. The fluid can include a plurality of non-clustered particles and a plurality of clustered particles. Each microwell can include a plurality of sidewalls and a bottom surface having a meshed trapping region. The meshed trapping region can be configured to capture the plurality of clustered particles and pass the plurality of non-clustered particles. The outputted fluid can include the plurality of non-clustered particles and can be substantially free of the plurality of clustered particles.

In any of the embodiments disclosed herein, the fluid can be blood, the non-clustered particles can include non-clustered cells, and the clustered particles can include cell-clusters.

In any of the embodiments disclosed herein, the fluid can be urine, the non-clustered particles can include non-clustered cells, and the clustered particles can include cell-clusters.

In any of the embodiments disclosed herein, the device can be configured to provide a volumetric flow rate through the inlet and outlet of between approximately 20 mL/hour and approximately 100 mL/hour.

In any of the embodiments disclosed herein, each microwell can have a depth of between approximately 10 microns and approximately 500 microns.

In any of the embodiments disclosed herein, at least a portion of each sidewall can be slanted.

In any of the embodiments disclosed herein, the device can include between approximately 40 and approximately 280 microwells per millimeter squared.

In any of the embodiments disclosed herein, the meshed trapping region can include one or more barrier lines.

In any of the embodiments disclosed herein, the one or more barrier lines can define a plurality of apertures.

In any of the embodiments disclosed herein, the plurality of apertures can divide a flow of the fluid into a plurality of flow paths.

In any of the embodiments disclosed herein, the plurality of apertures can be arranged in an array.

In any of the embodiments disclosed herein, each aperture of the plurality of apertures can be sized such that the non-clustered particles can pass through the apertures and the clustered particles cannot pass through the apertures.

In any of the embodiments disclosed herein, each aperture of the plurality of apertures can be square-shaped. Each square-shaped aperture of the plurality of apertures can have a side length of between approximately 10 microns and approximately 17 microns.

In any of the embodiments disclosed herein, each aperture of the plurality of apertures can be circular-shaped.

In any of the embodiments disclosed herein, each aperture of the plurality of apertures can be ellipsoid-shaped.

In any of the embodiments disclosed herein, each aperture of the plurality of apertures can be polygonal-shaped.

In any of the embodiments disclosed herein, each aperture of the plurality of apertures can have the same shape.

In any of the embodiments disclosed herein, the clustered particles can be label-free.

In any of the embodiments disclosed herein, the clustered particles can be labeled.

In any of the embodiments disclosed herein, the device can have a diameter of between approximately 5 millimeters and approximately 300 millimeters.

In any of the embodiments disclosed herein, the device can include a fluorine-based polymer.

In any of the embodiments disclosed herein, the device can include a perfluoropolyether-based polymer.

In any of the embodiments disclosed herein, the device can include a heat-curable polymer.

In any of the embodiments disclosed herein, the device can include a UV-curable polymer.

In any of the embodiments disclosed herein, the device can include a metal.

In any of the embodiments disclosed herein, the device can include a semiconductor.

The disclosed technology can also include a method of fabricating an isolation device for isolating clustered particles including fabricating a silicon mold on a silicon wafer; fabricating a polymer mold; fabricating the isolation device; and releasing the isolation device.

In any of the embodiments disclosed herein, fabricating the silicon mold on the silicon wafer can include depositing a first photoresist layer on the silicon wafer; patterning the first photoresist layer; etching the silicon wafer to form a plurality of pillars; depositing a nitride layer on the silicon wafer; depositing a second photoresist layer; patterning the second photoresist layer and the nitride layer; etching the silicon wafer to form slanted sidewalls extending to each pillar of the plurality of pillars; depositing a third photoresist layer; patterning the third photoresist layer; and etching the silicon wafer to form the silicon mold.

In any of the embodiments disclosed herein, fabricating the polymer mold can include coating the silicon wafer with silane; depositing a first polymer layer on the silicon wafer; curing the first polymer layer to form a first polymer mold; removing the first polymer mold from the silicon wafer; coating the first polymer mold with silane; depositing a second polymer layer on the first polymer mold; and curing the second polymer layer to form the second polymer mold.

In any of the embodiments disclosed herein, the first polymer layer and the second polymer layer can include polydimethylsiloxane (PDMS).

In any of the embodiments disclosed herein, fabricating the polymer mold can further include removing the second polymer mold from the first polymer mold.

In any of the embodiments disclosed herein, fabricating the isolation device can include affixing the second polymer mold to a substrate; filling the second polymer mold with a UV-curable polymer; exposing the UV-curable polymer to UV light; and curing the UV-curable polymer.

In any of the embodiments disclosed herein, a vacuum pump can be used to fill the second polymer mold with the UV-curable polymer.

In any of the embodiments disclosed herein, the substrate can be a vinyl dicing tape.

In any of the embodiments disclosed herein, the substrate can be an acetate sheet.

In any of the embodiments disclosed herein, the substrate can be a PET sheet.

In any of the embodiments disclosed herein, filling the second polymer mold with the heat-curable polymer can be performed on a thermoelectric cooler.

In any of the embodiments disclosed herein, the UV-curable polymer can be a heat-curable polymer.

In any of the embodiments disclosed herein, releasing the isolation chip can include removing the second polymer mold; and removing the isolation chip from the substrate.

The disclosed technology can also include a method for isolating clustered particles including providing an isolation device including a plurality of microwells where each microwell can have a plurality of sidewalls and a bottom surface with a meshed trapping region; passing a fluid through the isolation device, the fluid including a plurality of clustered particles and a plurality of non-clustered particles; capturing the plurality of clustered particles within the meshed trapping region; and outputting the fluid, the outputted fluid including the plurality of non-clustered particles.

In any of the embodiments disclosed herein, the fluid can be blood, the non-clustered particles can be cells, and the clustered particles can be cell-clusters.

In any of the embodiments disclosed herein, the fluid can be urine, the non-clustered particles can be cells, and the clustered particles can be cell-clusters.

In any of the embodiments disclosed herein, the method of isolating clustered particles can further include positioning the isolation device within a filtration holder.

In any of the embodiments disclosed herein, passing the fluid through the isolation device can occur a flow rate of between approximately 20 mL/hour and approximately 100 mL/hour.

In any of the embodiments disclosed herein, the outputted fluid can be substantially free of clustered particles.

In any of the embodiments disclosed herein, the method for isolating clustered particles can further include retrieving the clustered particles from the meshed trapping region.

In any of the embodiments disclosed herein, retrieving the clustered particles from the meshed trapping region can include washing the clustered particles with PBS and transferring the cell clusters to a holding container.

In any of the embodiments disclosed herein, a micromanipulator can retrieve the cell clusters directly from the meshed trapping region.

In any of the embodiments disclosed herein, the method for isolating clustered particles can further include analyzing the cells clusters.

In any of the embodiments disclosed herein, the clustered particles can include circulating tumor cell clusters.

In any of the embodiments disclosed herein, the clustered particles can include exfoliated cancer cells in urine.

In any of the embodiments disclosed herein, the method for isolating clustered particles can further include coating the isolation device with a growth culture.

In any of the embodiments disclosed herein, the captured clustered particles can grow on the coated isolation device.

In any of the embodiments disclosed herein, the grown clustered particles can be analyzed directly on the coated isolation device.

In any of the embodiments disclosed herein, the method for isolating clustered particles can further include coating the isolation device with an inorganic material.

In any of the embodiments disclosed herein, the method for isolating clustered particles can further include coating the isolation device with an organic material.

The disclosed technology can further include a method of filtering an unprocessed sample of blood using the device of claim 1.

The disclosed technology can further include a method of in-line filtering a sample of blood using the device of claim 1.

The disclosed technology can further include a method of detecting a clot using the device of claim 1.

The disclosed technology can further include a method of dissociating a clustered particle using the device of claim 1.

These and other aspects of the present invention are described in the Detailed Description below and the accompanying figures. Other aspects and features of embodiments of the present invention will become apparent to those of ordinary skill in the art upon reviewing the following description of specific, exemplary embodiments of the present invention in concert with the figures. While features of the present invention may be discussed relative to certain embodiments and figures, all embodiments of the present invention can include one or more of the features discussed herein. Further, while one or more embodiments may be discussed as having certain advantageous features, one or more of such features may also be used with the various embodiments of the invention discussed herein. In similar fashion, while exemplary embodiments may be discussed below as device, system, or method embodiments, it is to be understood that such exemplary embodiments can be implemented in various devices, systems, and methods of the present invention

BRIEF DESCRIPTION OF THE FIGURES

Reference will now be made to the accompanying figures, which are not necessarily drawn to scale, and wherein:

FIGS. 4A-4D illustrate variations of a meshed trapping region of a microwell, according to some aspects of the present disclosure.

DETAILED DESCRIPTION

Figures 1A, 1B:
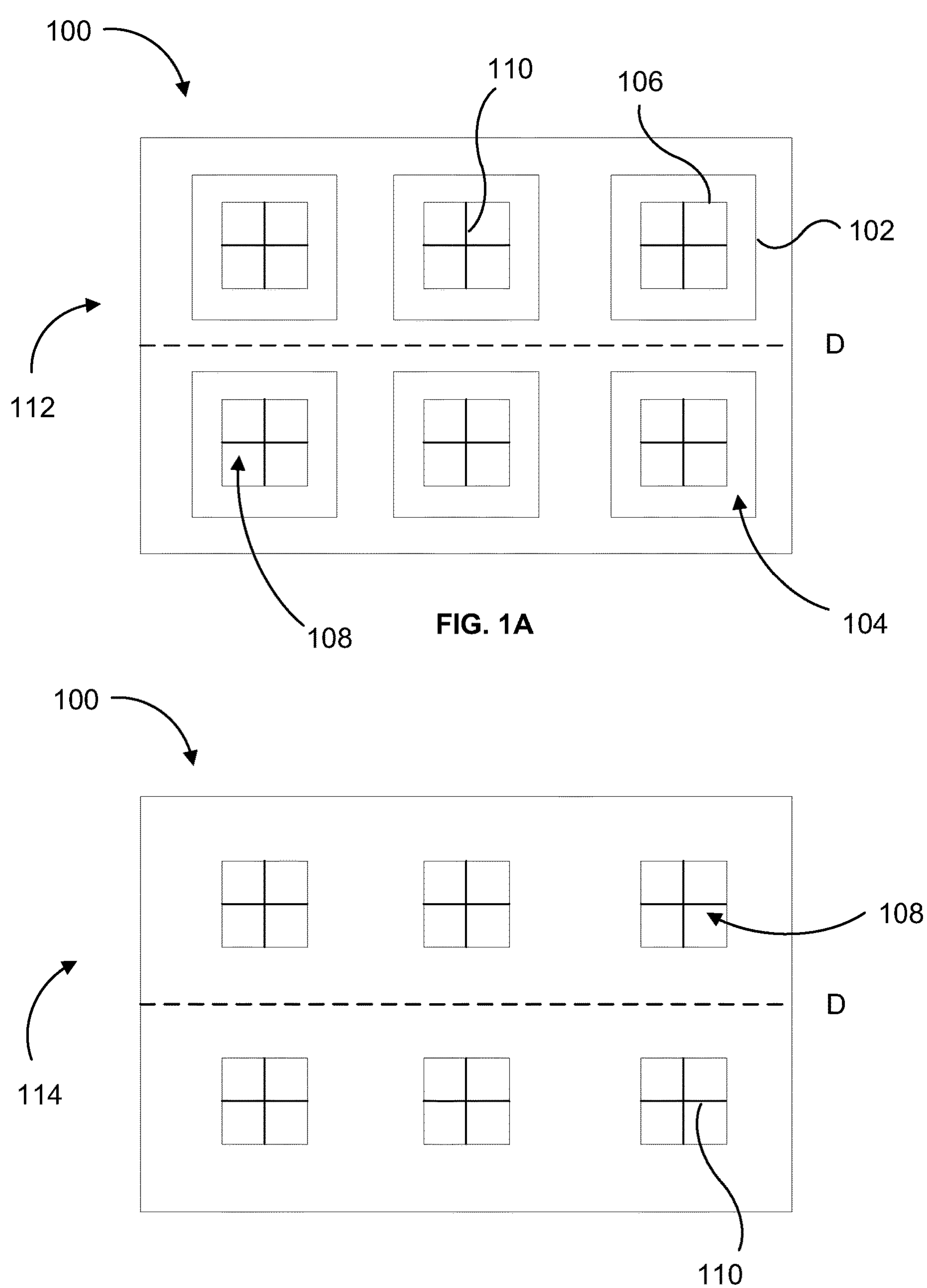
FIG. 1A is a top view of an isolation device, according to some aspects of the present disclosure.
FIG. 1B is a bottom view of an isolation device, according to some aspects of the present disclosure.

The present disclosure relates to an isolation device for isolating clustered particles from a sample of fluid including non-clustered particles and clustered particles. The isolation device can include a plurality of microwells having a bottom surface with a meshed trapping region. The meshed trapping region can be divided into a plurality of apertures using one or more barrier lines. The sample of fluid can be funneled into them microwells as the sample is passed through the isolation device at a high volumetric flow rate. The apertures can be sized such that the non-clustered particles can pass through the apertures, while the clustered particles are gently captured within the meshed trapping region. Once captured, the clustered particles can be retrieved from the meshed trapping region for further molecular and functional analysis. By isolating and analyzing the captured clustered particles valuable diagnostic information and insight on potential courses of treatment can be obtained.

The disclosed technology will be described more fully hereinafter with reference to the accompanying drawings. This disclosed technology can, however, be embodied in many different forms and should not be construed as limited to the examples set forth herein. The components described hereinafter as making up various elements of the disclosed technology are intended to be illustrative and not restrictive. Many suitable components that would perform the same or similar functions as components described herein are intended to be embraced within the scope of the disclosed electronic devices and methods. Such other components not described herein may include, but are not limited to, for example, components developed after development of the disclosed technology.

In the following description, numerous specific details are set forth. But it is to be understood that examples of the disclosed technology can be practiced without these specific details. In other instances, well-known methods, structures, and techniques have not been shown in detail in order not to obscure an understanding of this description. References to "one embodiment," "an embodiment," "example embodiment," "some embodiments," "certain embodiments," "various embodiments," etc., indicate that the embodiment(s) of the disclosed technology so described may include a particular feature, structure, or characteristic, but not every embodiment necessarily includes the particular feature, structure, or characteristic. Further, repeated use of the phrase "in one embodiment" does not necessarily refer to the same embodiment, although it may.

Throughout the specification and the claims, the following terms take at least the meanings explicitly associated herein, unless the context clearly dictates otherwise. The term "or" is intended to mean an inclusive "or." Further, the terms "a," "an," and "the" are intended to mean one or more unless specified otherwise or clear from the context to be directed to a singular form.

Unless otherwise specified, the use of the ordinal adjectives "first," "second," "third," etc., to describe a common object, merely indicate that different instances of like objects are being referred to, and are not intended to imply that the objects so described should be in a given sequence, either temporally, spatially, in ranking, or in any other manner.

Unless otherwise specified, the terms "clustered particle" and "clustered particles" mean any cluster of two or more particles, including microparticles and nanoparticles.

Unless otherwise specified, the terms "cell-clusters" include any cluster of two or more cells, where the cells can be of any type, including but not limited to, circulating tumor cells, exfoliated tumor cells, red blood cells, and artificially synthesized nanoparticle and microparticles.

FIG. 1A is a top view of an isolation device 100. The isolation device 100 can have an inlet 112 configured to receive a fluid. The isolation device 100 can include a plurality of microwells 102 configured to capture clustered particles. The microwells 102 can be recessed indentations of the isolation device 100. The microwells 102 can include a plurality of sidewalls 104. The sidewalls 104 can extend from the top surface to a bottom surface of the microwells 102. The microwells 102 can have a depth of any size. The depth of the microwell 102 can facilitate isolating and capturing clustered particles. The depth of the microwells 102 can be based upon the application in which the isolation device 100 is being used and the size of the clustered particle being captured by the isolation device 100. In some embodiments, the depth of the microwells 102 can be between approximately 10 microns and approximately 500 microns. In some embodiments, the isolation device 100 can be used to capture nanoparticle clustered particles or extracellular vesicle clustered particles. In this application, the depth of the microwell 102 can be submicron. The bottom surface of the isolation device 100 can include a meshed trapping region 106. A plurality of thin barrier lines 110 can divide the meshed trapping region 106 into a plurality of apertures 108.

FIG. 1B is a bottom view of the isolation device 100. The isolation device 100 can include an outlet 114 configured to output the fluid. The inlet 112 and the outlet 114 can be any type of inlet or outlet configured to deliver fluid to the microwells 102 and allowing fluid to exit the microwells 102. In some embodiments, the inlet 112 can be an open surface above the microwells 102. In some embodiments, the outlet 114 can be an open surface proximate the apertures 108 of the meshed trapping region 106.

Figure 2:
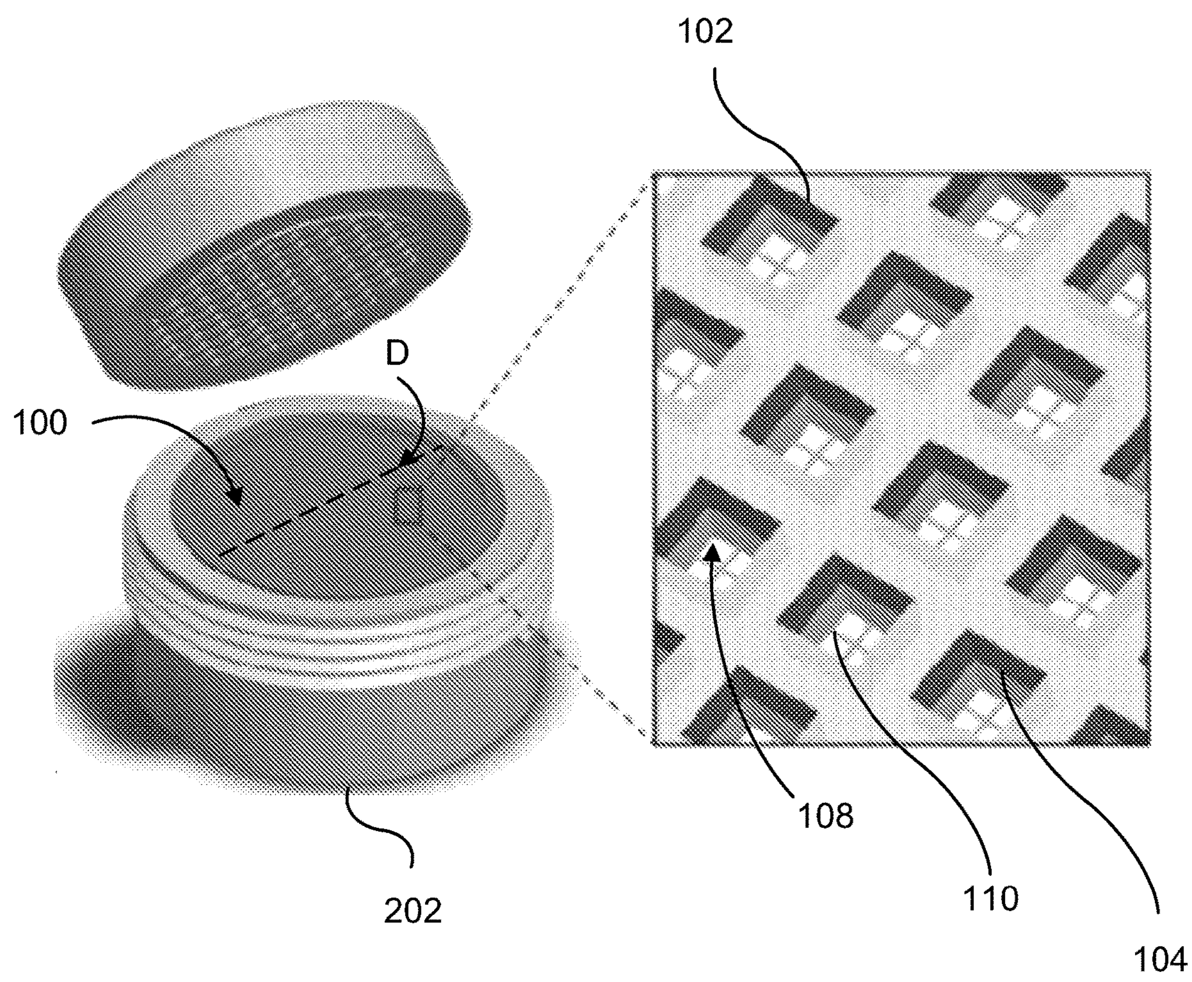
FIG. 2 is a diagram of an isolation device within a filtration holder, according to some aspects of the present disclosure.

FIG. 2 illustrates the isolation device 100 positioned within a filtration holder 202. The filtration holder 202 can be any commercially available filtration holder. The filtration holder 202 can be customized based on the desired size and shape of the isolation device 100 and the application in which the isolation device 100 is being used.

The isolation device 100 can be of any size and of any shape. In some embodiments, the isolation device 100 can be substantially rectangular, as illustrated in FIGS. 1A and 1B. In some embodiments, the isolation device 100 can be substantially circular, as illustrated in FIG. 2. The isolation device 100 can have a diameter D, as illustrated in FIGS. 1A, 1B and 2. The diameter D of the isolation device 100 in FIGS. 1A and 1B can be the length of the isolation device 100 with respect to a longitudinal axis. The diameter D can be based upon the diameter of the substrate, such as a silicon wafer, used during the method of fabricating the isolation device 100. The isolation device 100 can have a diameter D of between approximately 5 millimeters and approximately 300 millimeters. The diameter D of the isolation device 100 can be based upon the application in which the isolation device 100 is being used. In applications requiring a volumetric flow rate of greater than 1000 mL/hour, the isolation device 100 can have a greater diameter D as compared to applications requiring a volumetric flow rate of between 20 mL/hour and 100 mL/hour.

The rate at which the fluid can pass through the isolation device 100 can depend on the diameter D of the isolation device 100 and the application in which the isolation device 100 is to be used. In some embodiments, the fluid can pass through the isolation device 100 at a flow rate of between approximately 20 mL/hour and approximately 100 mL/hour. At this volumetric flow rate, the isolation device 100 can have a diameter D of approximately 25 millimeters or greater. and effectively isolate and capture clustered particles. In some embodiments, the fluid can pass through the isolation device 100 at a volumetric flow rate of greater than 1000 mL/hour. At this volumetric flow rate, the isolation device 100 can have a diameter D of approximately 150 mm to approximately 300 millimeters and effectively isolate and capture clustered particles.

The speed at which the fluid can pass through the isolation device 100 can similarly depend on the size of the isolation device 100 and the application in which the isolation device 100 is being used. In some embodiments, the fluid can pass through the isolation device 100 at a speed of between approximately 20 microns per second and approximately 260 microns per second.

The isolation device 100 can include any number of microwells 102. The number of microwells 102 can depend on the surface area of the isolation device 100. The number of microwells 102 can depend on the size of the clustered particle being isolated by the isolation device 100. In some embodiments, the isolation device 100 can have between approximately 40 and approximately 280 microwells per millimeter squared. When the isolation device 100 is being used to isolate nanoparticle clustered particles, the isolation device 100 can have between approximately 40,000 and approximately 280,000 microwells 102 per millimeter squared where each microwell 102 is sized with nanometer dimensions.

The isolation device 100 can be made of any material that can flow and subsequently solidify on demand and be micro-patterned and/or nano-patterned. In some embodiments, the isolation device 100 can be made substantially of a polymer. The polymer can be a UV-curable polymer. Alternatively or in addition to, the polymer can be a heat-curable polymer. The polymer can be a fluorine-based polymer, such as a perfluoropolyether-based polymer. A fluorine-based polymer can facilitate releasing of the isolation device 100 from various molds during the fabrication of the isolation device 100. In some embodiments, the isolation device 100 can be made substantially of a metal. In some embodiments, the isolation device can be made substantially of a semiconductor.

Figure 3A:
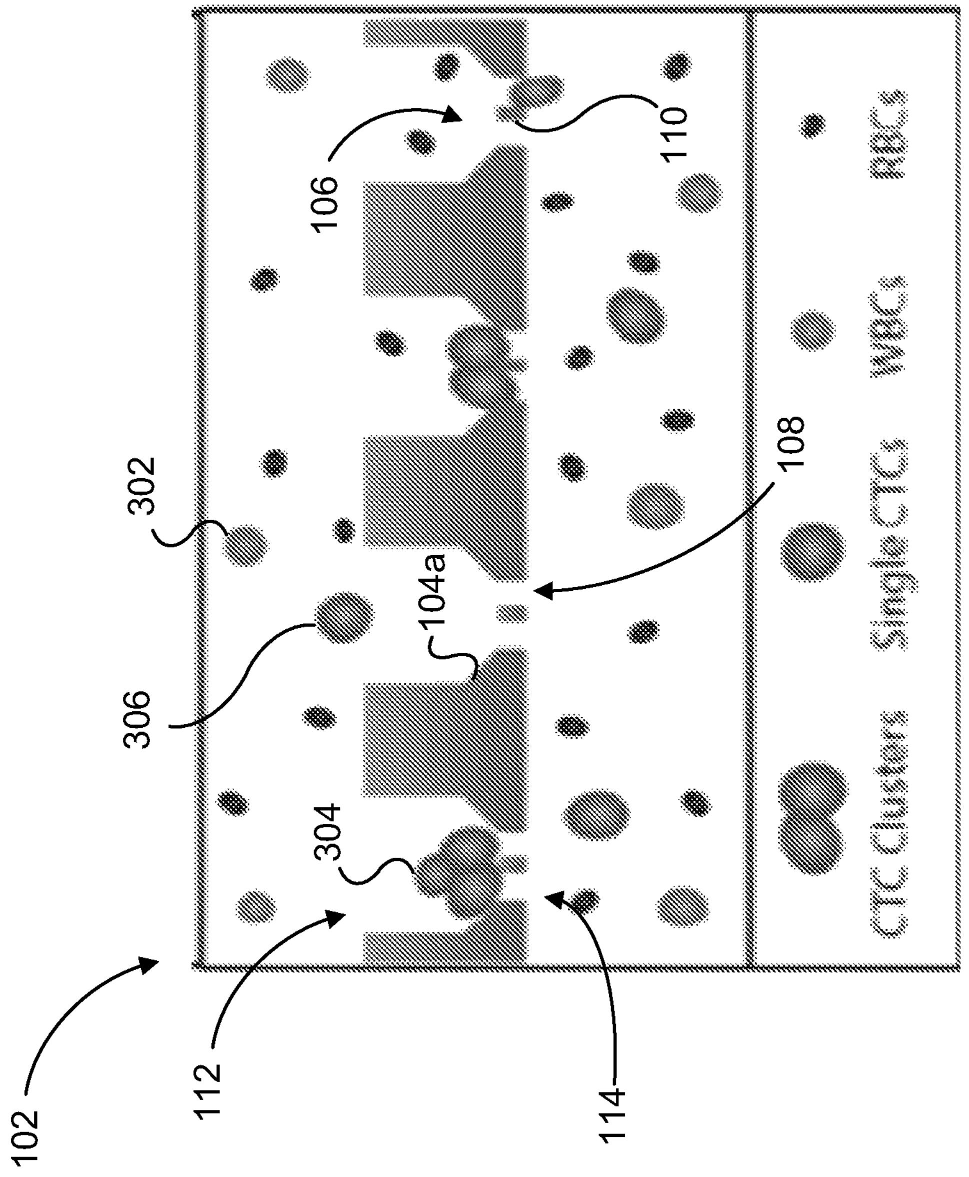
FIG. 3A is an illustration of a plurality of microwells of an isolation device, according to some aspects of the present disclosure.

FIG. 3A illustrates the plurality of microwells 102 of the isolation device 100. A sample of fluid can be passed through the inlet 112 of the isolation device 100. The fluid can include a plurality of non-clustered particles 302 and a plurality of clustered particles 304. The fluid can vary depending on the application in which the isolation device 100 is being used. In some embodiments the fluid can be blood. Alternatively, in some embodiments the fluid can be urine. The non-clustered particles 302 can include non-clustered cells, such as single red blood cells and white blood cells. In some embodiments, the non-clustered particles 302 can include single cancerous cells 306, such as single circulating tumor cells. The clustered particles 304 can include cell-clusters. The clustered particles 304 can be any number of cells clustered together, including but not limited to, 2 cell-clusters, 3 cell-clusters, and 10 cell-clusters. The clustered particles 304 can be label-free. Alternatively, the clustered particles 304 can be labeled. The labeling can include molecular labeling, such as fluorescence imaging, or bead-based labeling. The cell-clusters can be cancerous cell-clusters. By way of example, cell-clusters can include circulating tumor cell (CTC) clusters, ovarian cancer cell-clusters, breast cancer cell-clusters, prostate cell-clusters, and the like. In some embodiments, the cell-clusters can include a cluster of blood cells, indicating a potential blood clot. In some embodiments, the clustered particles 304 can include nanoparticle clustered particles. In some embodiments, the clustered particles 304 can include extracellular vesicle clusters.

As the sample of fluid is passed through the inlet 112 of the isolation device 100, the microwells 102 can funnel the non-clustered particles 302 and the clustered particles 304 into the meshed trapping region 106. As illustrated in FIG. 3A, the sidewalls 104 of the microwell 102 can have a slanted portion 104*a*. The slanted sidewalls 104*a* can be slanted at an angle of any degree, including a positive degree angle, a negative degree angle, and a zero-degree angle. The slanted sidewalls 104*a* can facilitate funneling the non-clustered particles 302 and the clustered particles 304 into the meshed trapping region 106. The slanted sidewalls 104*a* can also minimize movement of the captured clustered particle 304 such that the captured clustered particle 304 can remain securely within the microwell 102.

The barrier lines 110 creating the apertures 108 can divide the flow of the fluid into a plurality of flow paths. The apertures 108 can be sized depending on the application in which the isolation device 100 is being used and such that non-clustered particles 302 can pass through the apertures 108 and out the outlet 114. However, the geometric shape of the clustered particles 304 in relation to the size of the apertures 108 can prevent the clustered particles 304 from passing through the apertures 108. In some embodiments, the size of the apertures 108 can be between approximately 100 squared microns and 300 squared microns. In some embodiments, when the isolation device 100 is being used to capture nanoparticle clustered particles, the apertures 108 can be accordingly sized. The size of the apertures 108 can be optimized such that the microwell 102 can capture 2-cell and 3-cell clustered particles 304 while minimizing undesired capture of white blood cells. Because non-clustered particles 302 can easily pass through the apertures 108 without interference, the isolation device 100 can process large volumes of fluid, including unprocessed whole blood, without the risk of clogging the isolation device 100. By minimizing the risk of clogging, the isolation device 100 can be an ideal for clinical settings.

Figure 3B:
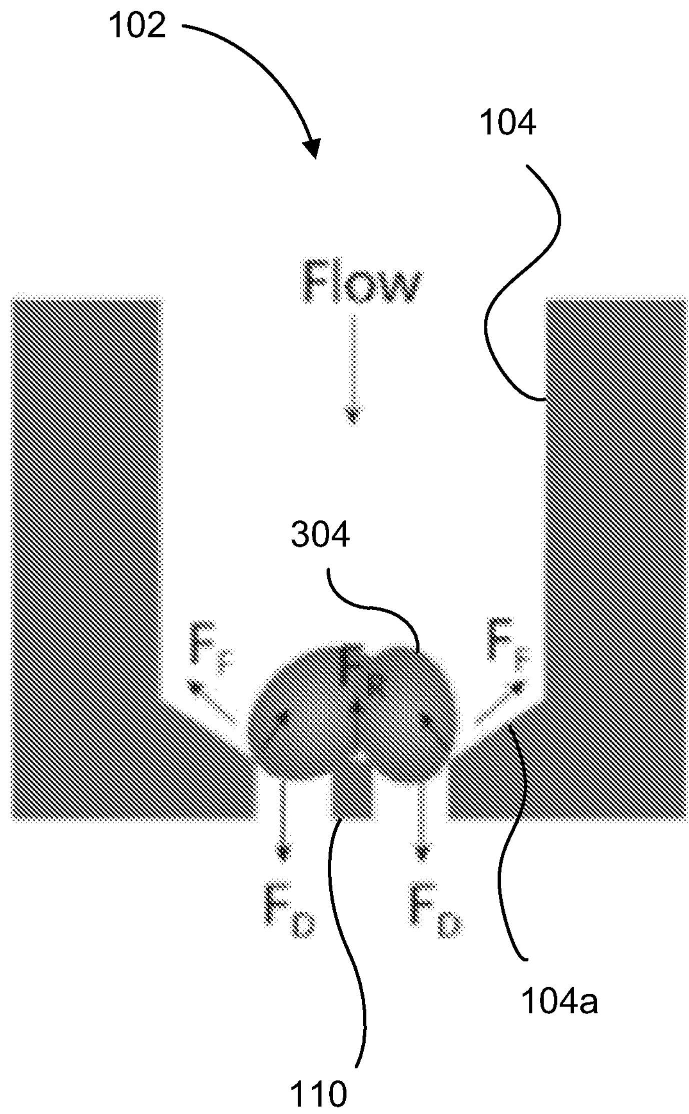
FIG. 3B is an illustration of forces acting upon a captured clustered particle, according to some aspects of the present disclosure.

FIG. 3B illustrates the forces that can act upon the clustered particle 304 within the meshed trapping region 106 of a microwell 102. A Dean drag force FD can be exerted due to flow of the sample of fluid as fluid passes through the microwell 102. When a clustered particle 304 engages with the barrier lines 110 of the meshed trapping region 106, a reaction force FR can be created. The reaction force FR can form a dynamic force balance that can provide a stable equilibrium for the captured clustered particle 304. Additionally, when the clustered particle 304 engages with the slanted sidewalls 104*a*, a friction force $F_F$ can be created. The combination of these forces can allow the microwell 102 to gently secure the clustered particle 304 without the clustered particle 304 dissociating.

Figure 3C:
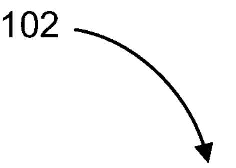
FIG. 3C is an illustration of a microwell having a captured clustered particle, according to some aspects of the present disclosure.
Figure 3C:
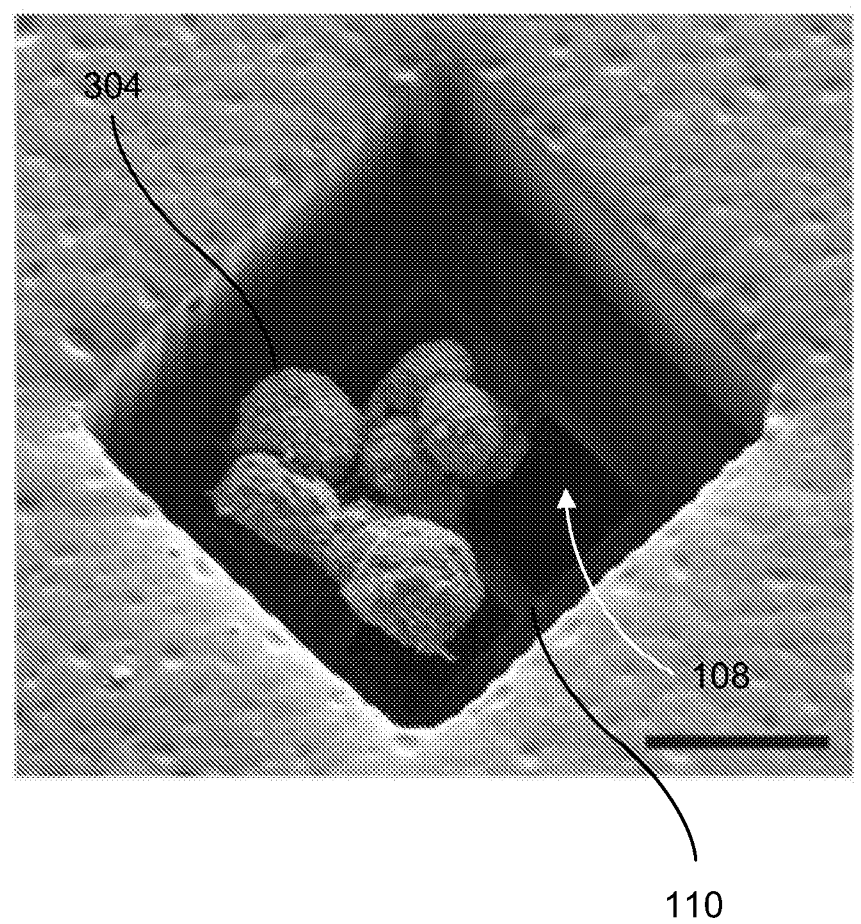

FIG. 3C is an additional illustration of the clustered particle 304 captured within the microwell 102. The configuration of the meshed trapping region 106 can allow the microwell 102 to gently capture the clustered particles 304. This gentle capture can minimize dissociation of the clustered particles 304. Because clustered particles 304 can be relatively rare within a sample of fluid and can provide valuable information upon analysis, it can be critical to prevent clustered particles 304 from dissociating.

FIGS. 4A through 4D illustrate various configurations of the meshed trapping region 106. Each meshed trapping region 106 can include one or more barrier lines 110 configured to divide the meshed trapping region 106 into a plurality of apertures 108 and to support a captured clustered particle 304. As illustrated in FIG. 4A, the barrier lines 110 can divide the meshed trapping region 106 into four apertures 108 having a square shape. The apertures 108 can be arranged in a 2 by 2 array. In some embodiments, each square aperture 108 can have a side length of between approximately 10 microns and approximately 17 microns. As illustrated in FIG. 4B, the meshed trapping region 106 can be divided into four apertures 108 having a substantially circular shape. As illustrated in FIG. 4C, the meshed trapping region 106 can be divided into four apertures 108 having a substantially ellipsoid shape. As illustrated in FIG. 4D, the meshed trapping region 106 be divided into five apertures 108 having a substantially polygonal shape. In some embodiments, each aperture 108 can have a hexagonal shape.

Although FIGS. 4A through 4D illustrate example variations of the meshed trapping region 106, it is contemplated that the meshed trapping region 106 can include any number of barrier lines 110 to create any number of apertures 108 having any geometric shape. The size and shape of the apertures 108 can be based upon the size and shape of the clustered particle 304, and the application in which the isolation device 100 is to be used. In some embodiments, the apertures 108 can have the same geometric shape and size. In some embodiments, the apertures 108 can have different geometric shapes and sizes. When the isolation device 100 is being used to capture nanoparticle clustered particles and/or extracellular vesicle clustered particles, the size of the apertures 108 can accordingly be sized.

FIGS. 5A through 8B illustrate cross-sectional and top views of example configurations of the plurality of microwells 102.

Figures 5A, 5B, 6A, 6B:
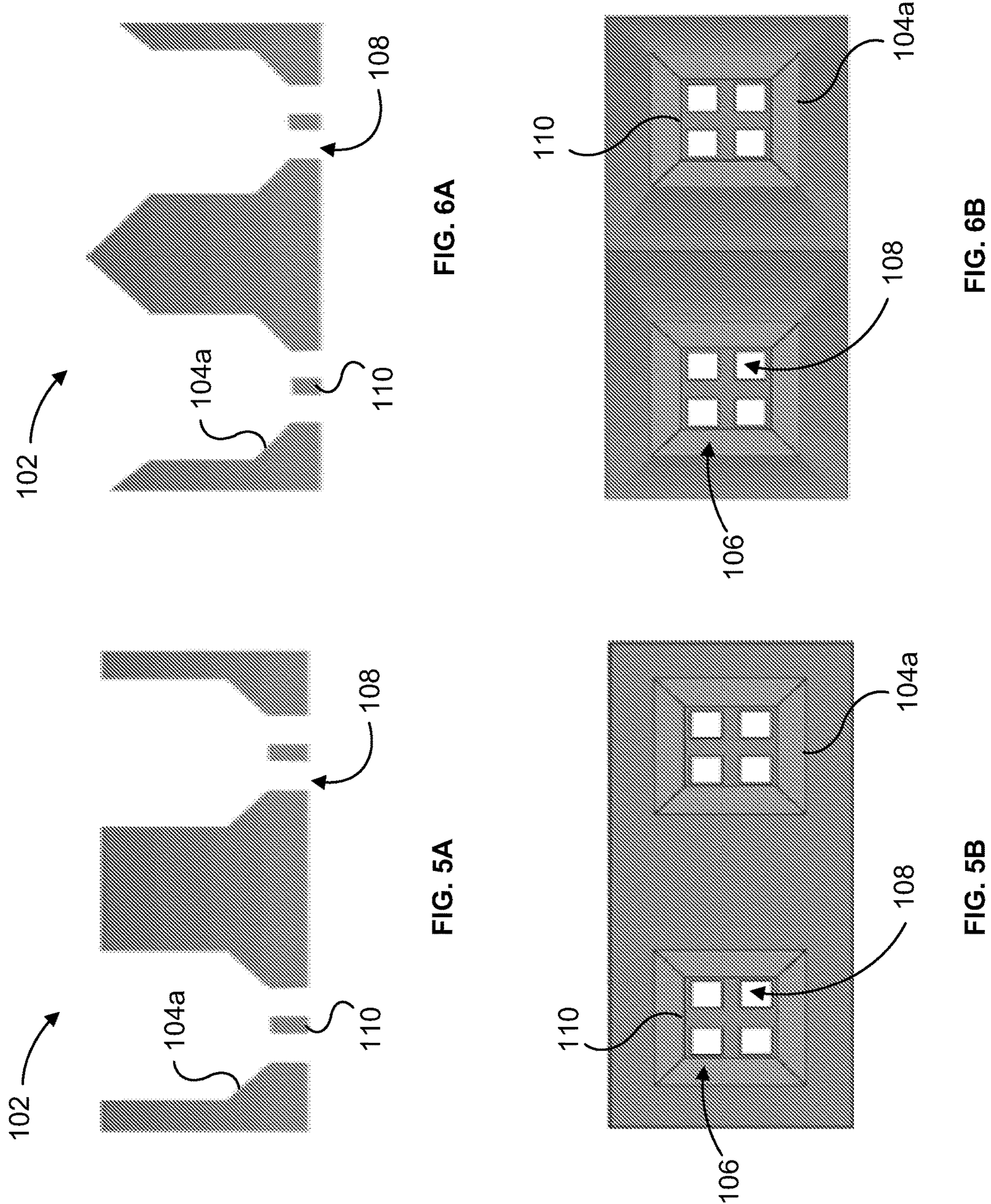
FIG. 5A illustrates a cross-section view of a plurality of microwells, according to some aspects of the present disclosure.
FIG. 5B illustrates a top view of the plurality of microwells of FIG. 5A, according to some aspects of the present disclosure.
FIG. 6A illustrates a cross-section view of a plurality of microwells, according to some aspects of the present disclosure.
FIG. 6B illustrates a top view of the plurality of microwells of FIG. 6A, according to some aspects of the present disclosure.

FIGS. 5A and 5B illustrate a cross-sectional view and top view, respectively, of a plurality of microwells 102. The microwells 102 can include slanted sidewalls 104*a* configured to funnel the fluid into the meshed trapping region 106. The barrier lines 110 can divide the meshed trapping region 106 into a plurality of square apertures 108 arranged in a 2 by 2 aperture array. The microwells 102 can be segregated from each by a flat portion of the top surface of the isolation device 100.

FIGS. 6A and 6B illustrate a cross-sectional view and top view, respectively, of a plurality of microwells 102 having a modified top portion as compared to the plurality of microwells illustrated in FIGS. 5A and 5B. Adjacent microwells 102 can be connected to one another such that a substantially pointed tip can be created. Barrier lines 110 can divide the meshed trapping region 106 of each microwell 102 into four square apertures 108 arranged in a 2 by 2 aperture array. The microwells 102 can include slanted sidewalls 104*a* to facilitate funneling and capturing the clustered particles 304 within the meshed trapping region 106.

Figures 7A, 7B, 8A, 8B:
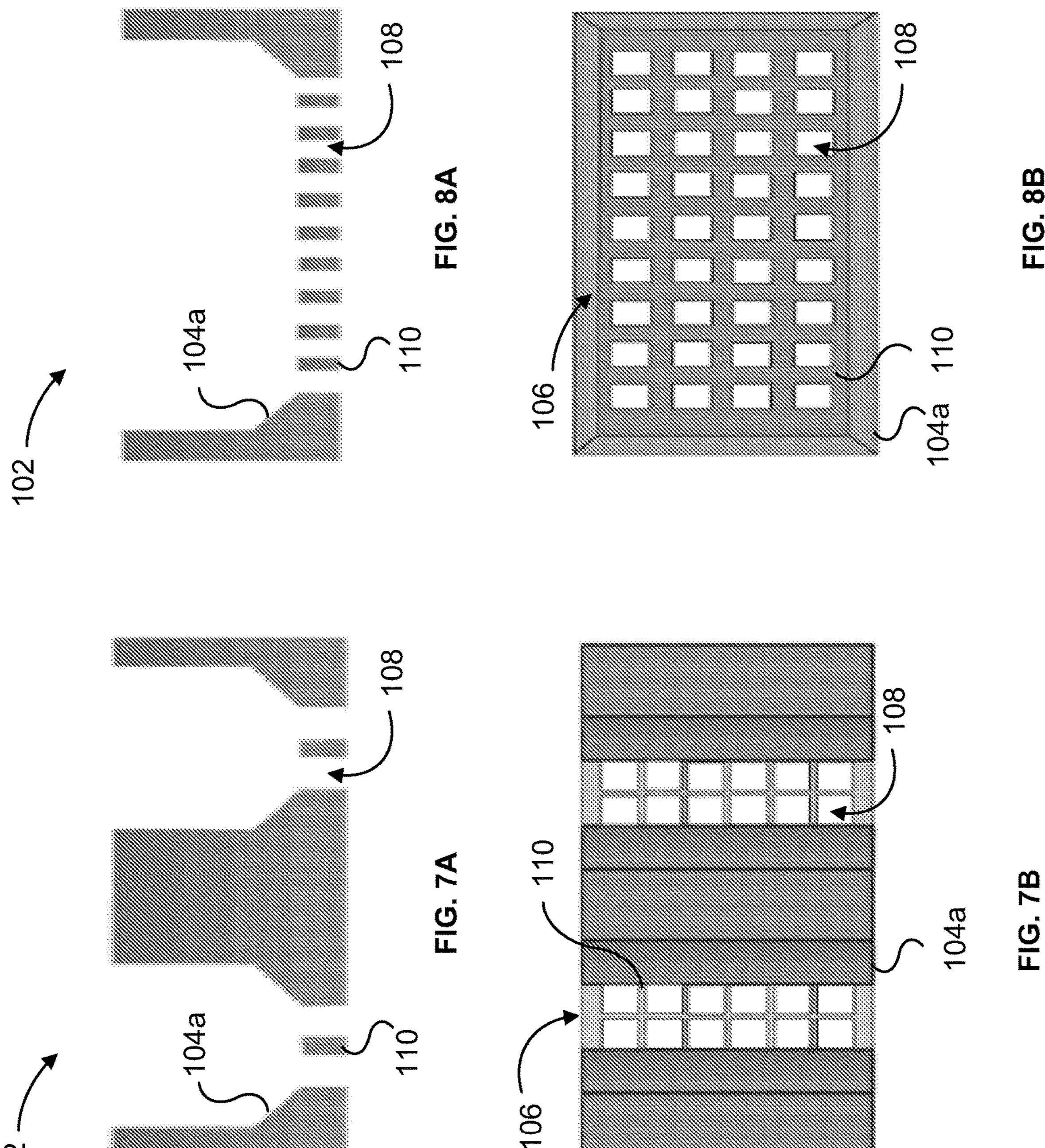
FIG. 7A illustrates a cross-section view of a plurality of microwells, according to some aspects of the present disclosure.
FIG. 7B illustrates a top view of the plurality of microwells of FIG. 7A, according to some aspects of the present disclosure.
FIG. 8A illustrates a cross-section view of a microwell, according to some aspects of the present disclosure.
FIG. 8B illustrates a top view of the microwell of FIG. 8A, according to some aspects of the present disclosure.

FIGS. 7A and 7B illustrate a cross-sectional view and top view, respectively, of a plurality of microwells 102 having a linear array of apertures 108. Barrier lines 110 can divide the meshed trapping region 106 of each microwell 102 into 12 apertures 108. The apertures 108 can be arranged in a 2 by 6 aperture array, such that the array is substantially linear. The microwells 102 can include slanted sidewalls 104*a* to facilitate funneling and capturing of the clustered particles 304 within the meshed trapping region 106. The microwells 102 can be segregated from each other by a flat portion of the top surface of the isolation device 100.

FIGS. 8A and 8B illustrate a cross-sectional view and top view, respectively, of a plurality of microwells 102 having a substantially meshed configuration. Barrier lines 110 can divide the meshed trapping region 106 of the microwell 102 into 36 apertures. The apertures 108 can be arranged in a 9 by 4 aperture array. The microwells 102 can include slanted sidewalls 104*a* to facilitate funneling and capturing of the clustered particles 304 within the meshed trapping region 106.

Although FIGS. 5A through 8B illustrate example variations of the microwells 102, it is contemplated that the microwells 102 can have any configuration. The meshed trapping region 106 can include any array of apertures 108. The array of apertures 108 can be any number of apertures by any number of apertures, including but not limited to, a 2 by 2 aperture array, a 3 by 5 aperture, a 4 by 6 aperture array, and a 5 by 10 aperture array.

Figure 9:
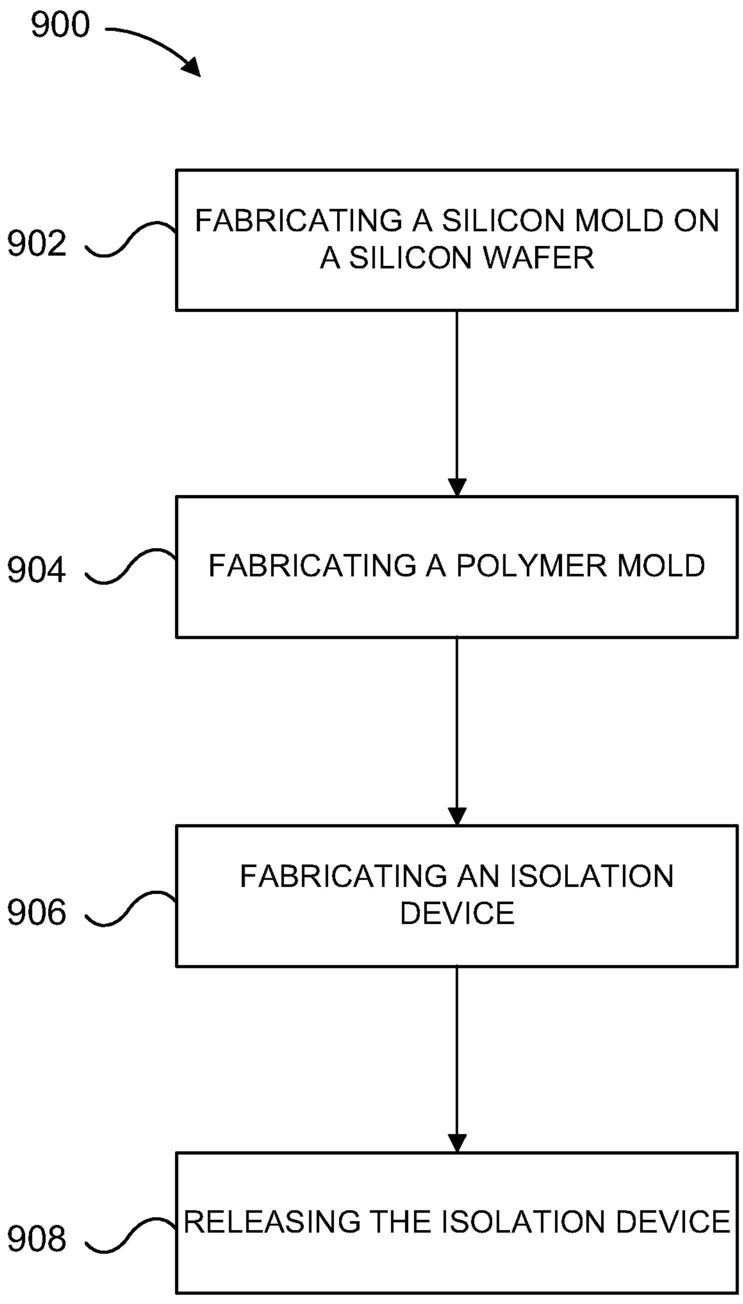
FIG. 9 is a flow diagram outlining the method of fabricating an isolation device, according to some aspects of the present disclosure.

The disclosed technology can also include a method 900 of fabricating an isolation device 100. As illustrated in FIG. 9, the method 900 can include fabricating 902 a silicon mold on a silicon wafer, fabricating 904 a polymer mold, fabricating 906 the isolation device, and releasing 908 the isolation device. The method 900 of fabricating the isolation device 100 can be performed in a cleanroom-free environment, thereby reducing costs and time of labor.

Figures 10A, 10B, 10C, 10D, 10E, 10F:
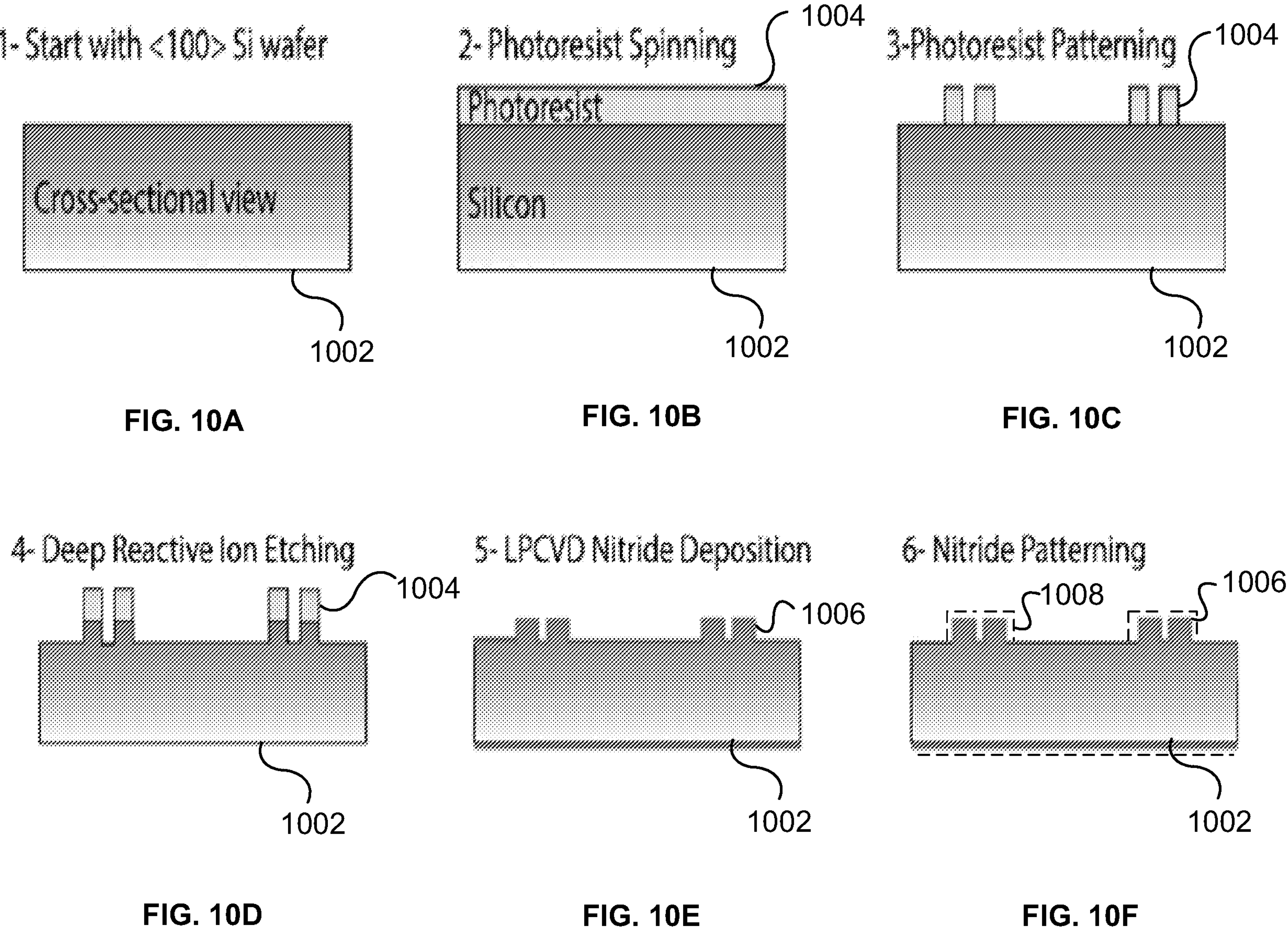
FIGS. 10A-10I illustrate a method of fabricating a silicon mold, according to some aspects of the present disclosure.

FIGS. 10A through 10I illustrate the method of fabricating the silicon mold 1012. A silicon wafer 1002 can be provided, as illustrated in FIG. 10A. In some embodiments, the silicon wafer 1002 can have a thickness of between approximately 300 microns and 600 microns.

In FIGS. 10B and 10C, a first photoresist layer 1004 can be deposited on the silicon wafer 1002. The photoresist layer 1002 can be spun and patterned. The patterned photoresist layer 1004 can be the foundation for the desired array of apertures 108 of the meshed trapping region 106.

In FIG. 10D, the silicon wafer 1002 can be etched to form pillars 1006. The silicon wafer 1002 can be etched approximately 10 microns deep using deep reactive ion etching.

In FIG. 10E, a nitride layer 1006 can be deposited. The nitride layer 1006 can be approximately 300 nanometers thick. The nitride layer 1006 can be deposited in a low-pressure chemical vapor deposition furnace. The nitride layer 1006 can be coated with a second photoresist layer 1008. As illustrated in FIG. 10F, the nitride layer 1006 and the second photoresist layer 1008 can be patterned. In some embodiments, the second photoresist layer 1008 can be exposed by maskless aligner.

Figures 10G, 10H, 10I:
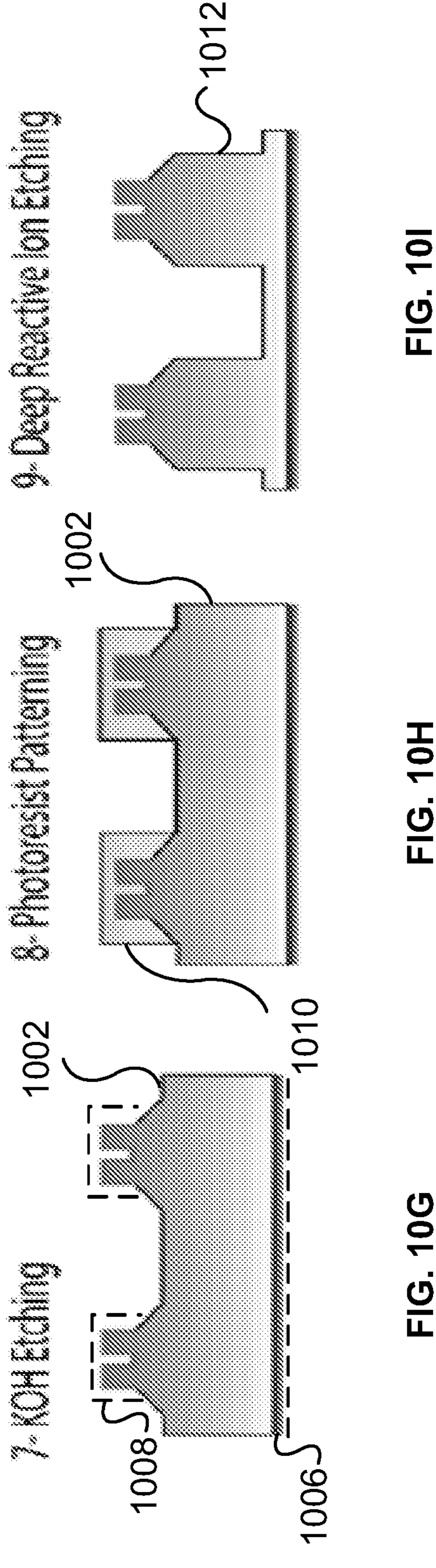

The nitride layer 1006 can be etched using reactive ion etching to form a hard mask and the silicon wafer 1002 can be anisotropically etched in a 45% KOH solution at approximately 80° C. for approximately 10 to 20 minutes, as illustrated in FIG. 10G. The etching of the silicon wafer 1002 can create slanted walls. The slanted walls can extend to the plurality of pillars. The formation of the slanted walls can be the foundation for creating the slanted sidewalls 104*a* of the isolation device 100.

A third photoresist layer 1010 can be deposited and patterned on the silicon wafer 1002, as illustrated in FIG. 10H. The silicon wafer 1002 can be etched approximately 50 microns deep using deep reactive ion etching. The etching of the silicon wafer 1002 can form the silicon mold 1012.

Figures 11A, 11B, 11C:
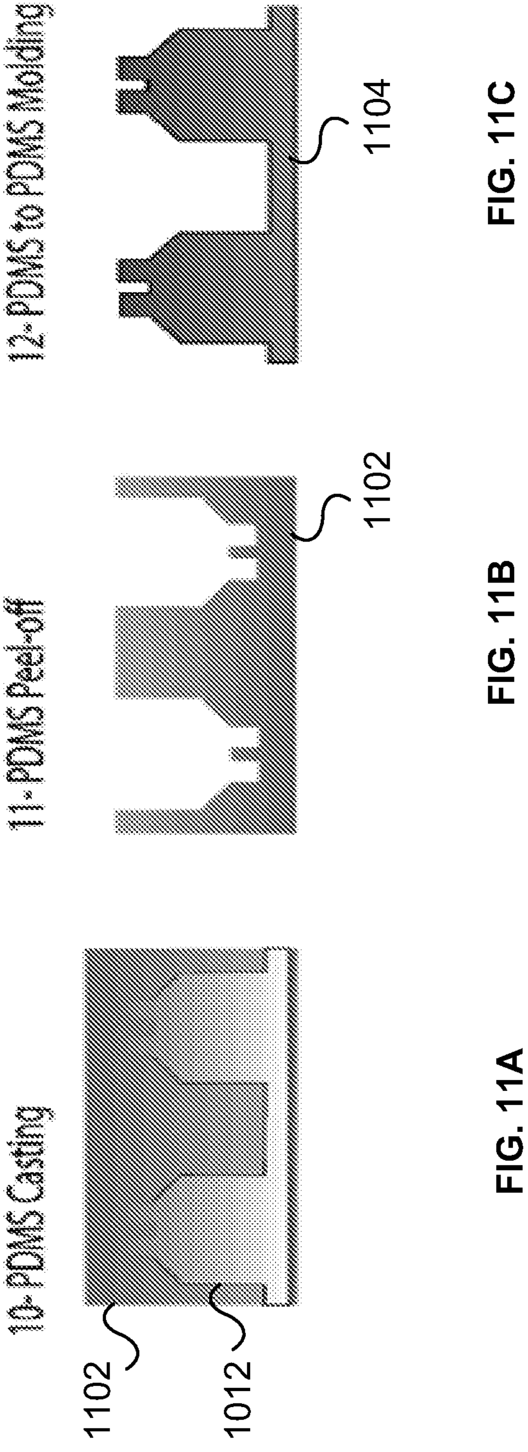
FIGS. 11A-11C illustrate a method of fabricating a polymer mold, according to some aspects of the present disclosure.

FIGS. 11A through 11C illustrate the method of fabricating the polymer mold. The method of fabricating the polymer mold can include double molding of a polymer. The silicon mold 1012 can be coated with silane under vacuum conditions for eight hours prior to fabricating the polymer mold. Coating the silicon mold 1012 with silane can facilitate removing the first polymer mold 1102 from the silicon mold 1012. In some embodiments, metal layer sputtering, including gold layer sputtering, can also be used to reduce and/or eliminate the eight hour waiting time. FIG. 11A illustrates fabrication of a first polymer mold 1102. A first polymer layer can be poured onto on the silicon mold 1012. The first polymer layer can be degassed in a desiccator for an hour and then cured in an oven to form the first polymer mold 1102. The cured first polymer mold 1102 can be peeled off from the silicon mold 1012, as illustrated in FIG. 11B. The surface of the first polymer mold 1102 can be activated using oxygen plasma and coated with silane for approximately eight hours. As illustrated in FIG. 11C, the first polymer mold 1102 can serve as the mold for the fabrication of a second polymer mold 1104. A second polymer layer can be poured over the first polymer mold 1102 and cured to form the second polymer mold 1104. Upon fabrication of the second polymer mold 1104, the second polymer mold 1104 can be removed from the first polymer mold 1102.

In some embodiments, the first polymer layer and the second polymer layer can include polydimethylsiloxane (PDMS).

Figures 12A, 12B, 12C:
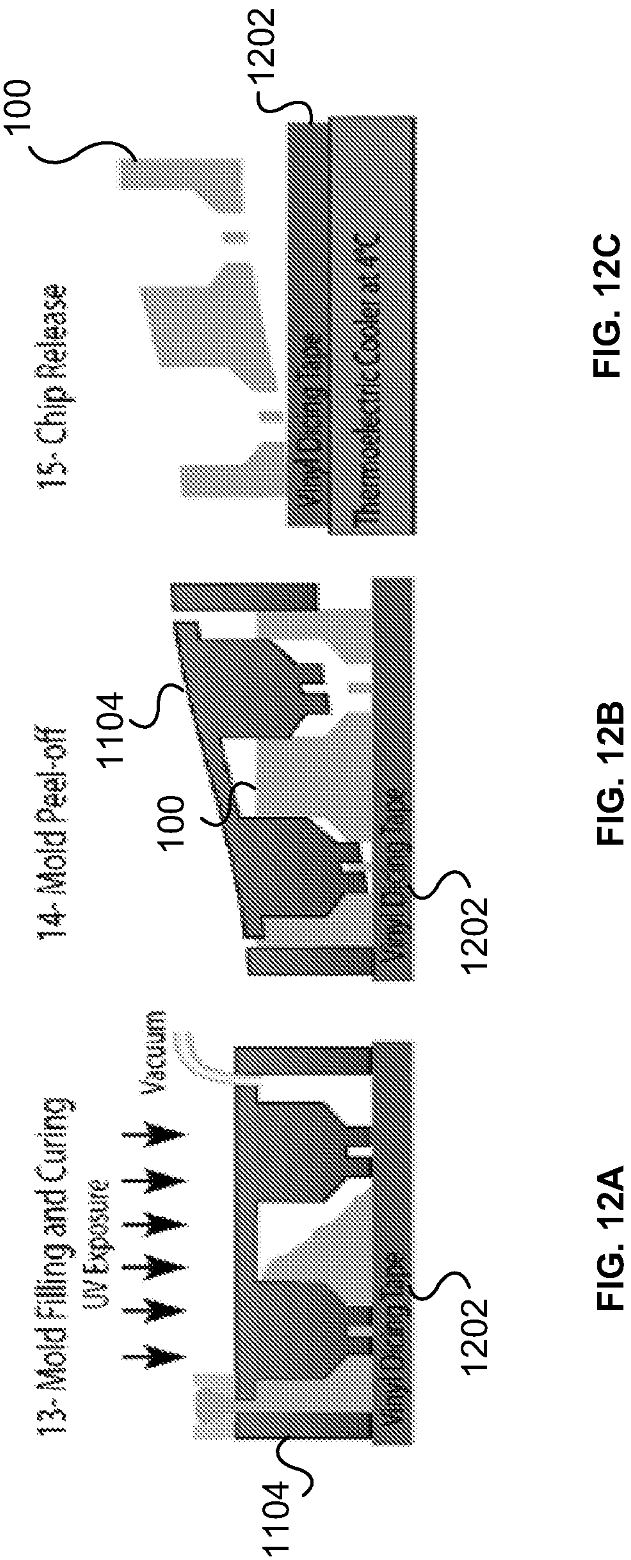
FIGS. 12A-12C illustrate a method of fabricating and releasing an isolation device, according to some aspects of the present disclosure.

FIGS. 12A through 12C illustrate the method of fabricating and releasing the isolation device 100. As illustrated in FIG. 12A, the second polymer mold 1104 can be affixed to a substrate 1202. In some embodiments, the second polymer mold 1104 can be affixed to a non-adhesive side of vinyl dicing tape. Alternatively, the substrate 1202 can include an acetate sheet, a PET sheet, or other similar materials. Upon affixing the second polymer mold 1104 to the substrate 1202, the second polymer mold 1104 can be filled with a UV-curable polymer. The UV-curable polymer can be inserted through an inlet of the second polymer mold 1104. A vacuum can be applied to an outlet port in order to facilitate filling the second polymer mold 1104 with the UV-curable polymer. Once the second polymer mold 1104 is filled with the UV-curable polymer, the UV-curable polymer can be exposed to UV light, thereby curing the UV-curable polymer to form the isolation device 100. In some embodiments, the UV light can have a wavelength of approximately 365 nanometers. In some embodiments, the second polymer mold 1104 can be filled with the UV-curable polymer on top of a thermoelectric cooler. The thermoelectric cooler can lower the temperature of the UV-curable polymer, thereby increasing the viscosity of the UV-curable polymer. By increasing the viscosity of the UV-curable polymer, higher vacuum levels can be used without generating bubbles, resulting in enhanced fabrication yield.

As illustrated in FIG. 12B, once the UV-curable polymer has been cured, the second polymer mold 1104 can be peeled off from the isolation device 100. The isolation device 100 can then be released from the substrate 1202, as illustrated in FIG. 12C. In some embodiments, the isolation device 100 can be positioned on the thermoelectric cooler to facilitate the release of the isolation device 100.

In some embodiments, the UV-curable polymer can be a fluorine-based polymer, including a perfluoropolyether-based polymer. In some embodiments, the UV-curable polymer can be a heat-curable polymer. By way of example, when exposure to UV light is not desired, a heat-curable polymer such as PDMS can be used to form the isolation device 100.

Although FIGS. 10A through 12C illustrate one example method of fabricating the isolation device 100, other methods are contemplated. In some embodiments, hot embossing can be used for fabricating an isolation device 100 made substantially of a polymer. Hot embossing can be a low cost and scalable technique for fabricating the isolation device 100, thereby rendering this technique applicable to a wide range of applications. In this technique, the polymer can include polymethylmethacrylate, cyclic olefin copolymer, polycarbonate, polyethylene and the like. The technique can generally include heating, molding, and demolding. The polymer can be softened by heating the polymer above the polymer's glass transition temperature. Pressure can be applied such that the softened polymer can take the shape of an underlying mold. In the demolding step, the polymer can be cooled down and released from the mold. Through holes can then be punched through the polymer to create the apertures 108 of the isolation device 100. The temperature, pressure, and selection of the polymer can be varied depending on the application and desired parameters of the isolation device 100, such as thickness.

Additionally, in some embodiments, conventional and electroless electroplating can be used for fabricating an isolation device 100 made substantially of a metal. This technique can include fabricating the second polymer mold 1104 as described herein. A metal seed layer can be deposited on the surface of the second polymer mold 1104 using an e-beam evaporator at high vacuum. Metal ions can attach to the surface of the second polymer mold 1104 and subsequently grow. The grown metal can have substantially the same shape as the second polymer mold 1104. The strength and flexibility of the isolation device 100 can be varied by changing the thickness of the electroplated metal.

In some embodiments, silicon micromachining can be used to fabricate the isolation device 100. Unlike the fabrication method illustrated in FIGS. 10A-12C that is capable of being performed without a cleanroom, silicon micromachining can fabricate the isolation device 100 from a silicon wafer within a cleanroom. For this technique, a silicon nitride layer can be deposited on the silicon wafer. The silicon nitride layer can be patterned using reactive ion etching and silicon wafer can be etched using a KOH (or TMAH) solution. Backside photolithography can be performed, and the nitride layer can subsequently be plasma etched to create the isolation device 100.

Figure 13:
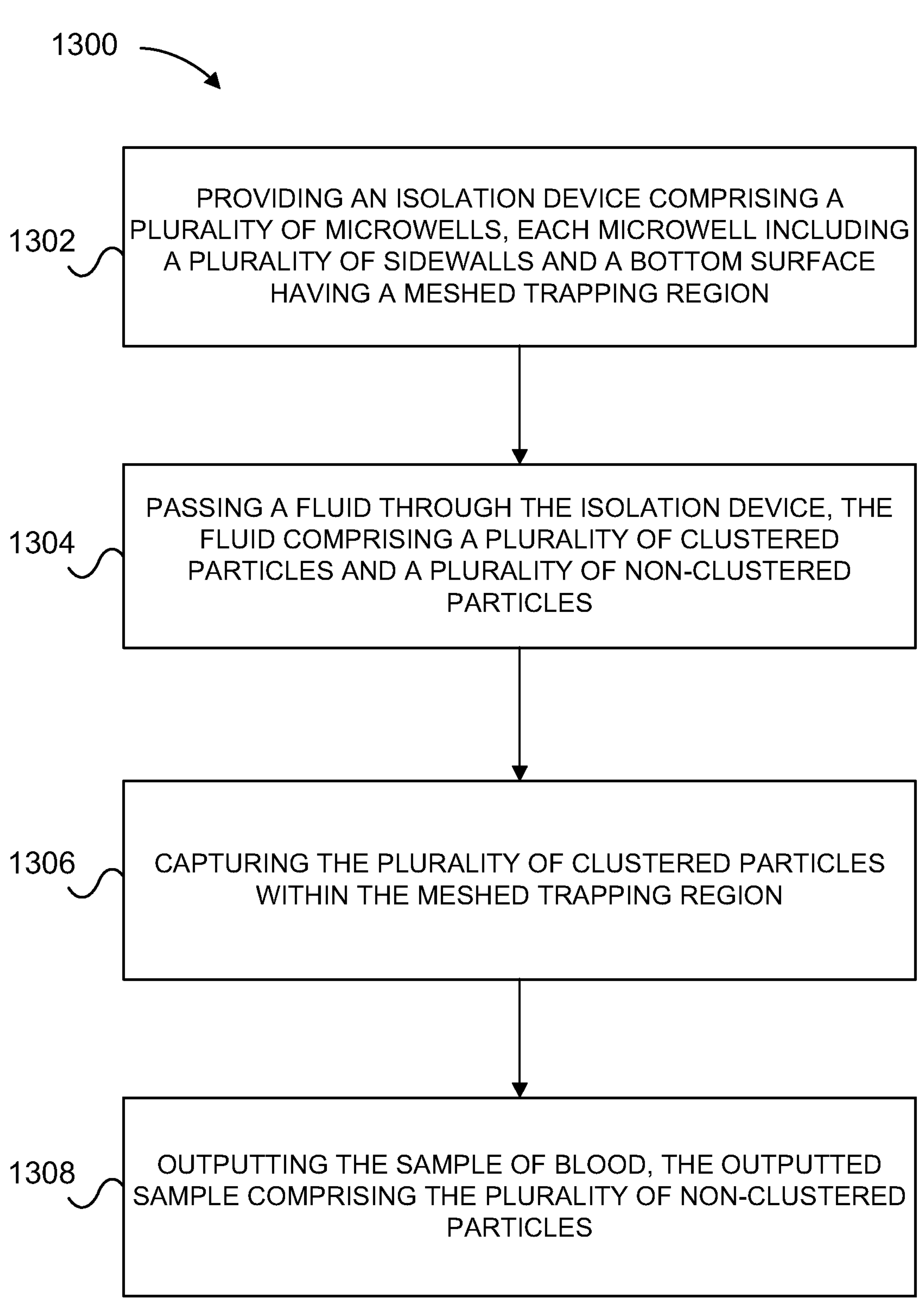
FIG. 13 illustrates a method of isolating clustered particles, according to some aspects of the present disclosure.

FIG. 13 illustrates a method 1300 of isolating clustered particles. The method 1300 can include providing 1302 an isolation device 100 comprising a plurality of microwells 102. Each microwell 102 can include a plurality of sidewalls 104 and a bottom surface having a meshed trapping region 106. The isolation device 100 can further include any of the features discussed herein.

The method 1300 can include passing 1304 a fluid through the isolation device 100. The fluid can include a plurality of non-clustered particles 302 and a plurality of clustered particles 304. As the fluid passes through the isolation device 100, the non-clustered particles 302 and the clustered particles 304 can be funneled into the microwells 102.

The method 1300 can include capturing 1306 the plurality of clustered particles 304 within the meshed trapping region 106.

The method 1300 can include outputting 1308 the sample of fluid. The outputted sample comprising the plurality of non-clustered particles 302. The outputted sample can be substantially free of clustered particles 304, as the clustered particles 304 can remain captured within the microwells 102.

The method 1300 can further include retrieving the clustered particles 304 from the meshed trapping region 106. To retrieve the clustered particles 304, the clustered particles 304 can be washed with PBS. Following the wash with PBS, the captured clustered particles 304 can be released at different relative reverse flow rates with respect to the volumetric flow rate at which the fluid flows through the isolation device 100. The released clustered particles 304 can then be transferred into a holding container. Alternatively, the clustered particles 304 can be retrieved directly from the meshed trapping region 106. In some embodiments, the clustered particles 304 can be retrieved directly from the meshed trapping region 106 using a micromanipulator. Unlike a traditional pore filter in which the captured clustered particles 304 can adhere to the surface of the filter, the recessed position of the meshed trapping region 106 within the microwell 102 can allow the isolation device 100 to be moved to a system or device configured for analysis without the risk of losing the captured clustered particles 304.

Retrieved clustered particles can be imaged and subjected to any form of molecular and function analysis. By analyzing the clustered particles 304, valuable information about the clustered particles 304 can be obtained, including origin of cancer and mutations of cells. Additionally, potential courses of treatment can be explored. In some embodiments, the clustered particles 304 can be treated with potential drugs and/or other forms of therapy. The results of these drug and therapy treatments can help improve personalized medicine.

In some embodiments, the method 1300 of isolating clustered particles can include coating the isolation device 100 with an organic coating or an inorganic coating. In some embodiments, an inorganic coating can increase the surface adhesion properties of the isolation device 100. The inorganic coating can include antibodies having a specific affinity such that the isolation device 100 can capture clustered particles 304. In some embodiments, an organic coating, such as a PEG or BSA coating, can reduce non-specific adhesion such that captured clustered particles 304 can be released.

In some embodiments, the method 1300 of isolating clustered particles can include coating the isolation device 100 with a growth culture. When the isolation device 100 is coated with a growth culture, the captured clustered particles 304 can be grown directly on the isolation device 100. In this sense, the isolation device 100 can function similar to a human organ and/or tissue. Because of the continuous flow of fluid (e.g. flow of blood) the captured clustered particles 304 can easily survive as the flow of fluid can provide a continuous source of nutrition. The grown clustered particles 304 can then be further analyzed by a variety of techniques. In some embodiments, the grown clustered particles 304 can be released and cultured for realization of new cell lines or development of new drug treatments.

The isolation device 100 and/or the method 1300 of isolating clustered particles can be used in a variety of additional applications. By way of example, urine cytology is a technique in which abnormal cells in urine can be examined under microscope to diagnose urinary tract cancers, including bladder cancer. This technique can require enrichment of rare exfoliated cancer cells from high volumes of voided urine samples attained from patients. Instead of using current centrifugation and cytospin methods, the isolation device 100 can be used to filter a large volume sample of urine without damaging or losing a substantial number of the rare exfoliated cancer cells. Upon capturing the exfoliated cancer cells, fluorescent and pap staining protocols can be used to characterize the cells.

In some embodiments, the isolation device 100 can be used to filter an unprocessed sample of blood. Additionally, the isolation device 100 can be used in an in-line blood purification system. Because circulating tumor cell clusters have a high metastatic propensity compared to individual circulating tumor cells, it can be critical to clean the blood from CTC clusters. In this application, blood can be removed from a patient. The blood can be directed through a blood pump and anticoagulant can be added. The blood can flow through the isolation device 100. The CTC clusters can become gently trapped within the microwells 102 of the isolation device 100 while the single red blood cells, white red blood cells, and single CTCs can pass through the isolation device 100. The cleaned blood being substantially free of CTC clusters can be directed back to the patient. This technique can be done continuously with a portable system and/or for a certain period of time with intervals in between according to the severity of the patient.

In some embodiments, the isolation device 100 can be used for breaking apart clustered particles. In this technique, the volumetric flow rate in which a sample of blood is passed through the isolation device 100 can be increased such that the shear force on the captured clustered particles also is increased. The increase in shear force can cause dissociation of the clustered particles 304 into non-clustered particles 302. By way of example, CTC clusters can be dissociated into single CTCs. Because single CTCs have been found to be less metastatic, this technique can facilitate therapeutic interventions and improve the treatment process.

It is to be understood that the embodiments and claims disclosed herein are not limited in their application to the details of construction and arrangement of the components set forth in the description and illustrated in the drawings. Rather, the description and the drawings provide examples of the embodiments envisioned. The embodiments and claims disclosed herein are further capable of other embodiments and of being practiced and carried out in various ways. Also, it is to be understood that the phraseology and terminology employed herein are for the purposes of description and should not be regarded as limiting the claims.

Accordingly, those skilled in the art will appreciate that the conception upon which the application and claims are based may be readily utilized as a basis for the design of other structures, methods, and systems for carrying out the several purposes of the embodiments and claims presented in this application. It is important, therefore, that the claims be regarded as including such equivalent constructions.

Furthermore, the purpose of the foregoing Abstract is to enable the United States Patent and Trademark Office and the public generally, and especially including the practitioners in the art who are not familiar with patent and legal terms or phraseology, to determine quickly from a cursory inspection the nature and essence of the technical disclosure of the application. The Abstract is neither intended to define the claims of the application, nor is it intended to be limiting to the scope of the claims in any way. Instead, it is intended that the invention is defined by the claims appended hereto.

What is claimed is:

1. A system comprising:

an isolation device formed by a fabricating process and comprising:

an inlet;

microwells, each microwell including sidewalls and a bottom surface having a meshed trapping region; and an outlet;

wherein the device is configured to:

receive a fluid through the inlet comprising non-clustered particles and clustered particles; and output an isolated fluid through the outlet comprising at least substantially all of the non-clustered particles and being at least substantially free of the clustered particles;

wherein the meshed trapping region is configured to capture at least substantially all clustered particles of the fluid and pass at least substantially all non-clustered particles of the fluid; and wherein the meshed trapping region comprises apertures configured to divide a flow of the fluid into flow paths.

2. The system of claim 1 further comprising the fluid;

wherein the fluid is blood, the non-clustered particles comprise non-clustered cells, and the clustered particles comprise cell-clusters.

3. The system of claim 1 further comprising the fluid;

wherein the fluid is urine, the non-clustered particles comprise non-clustered cells, and the clustered particles comprise cell-clusters.

4. The system of claim 1, wherein the device is further configured to provide a volumetric flow rate through the inlet and outlet of between approximately 20 mL/hour and approximately 100 mL/hour.

5. The system of claim 1, wherein each microwell has a depth of between approximately 10 microns and approximately 500 microns.

6. The system of claim 1, wherein at least a portion of each sidewall is slanted.

7. The system of claim 1, wherein the device comprises between approximately 40 and approximately 280 microwells per millimeter squared.

8. The system of claim 1, wherein the apertures are arranged in an array.

9. The system of claim 1, wherein each aperture is sized such that the non-clustered particles pass through the apertures and the clustered particles do not pass through the apertures.

10. The system of claim 1, wherein each aperture has a shape selected from the group consisting of a square, circle, ellipse, and polygon.

11. The system of claim 10, wherein each aperture is square-shaped having a side length of between approximately 10 microns and approximately 17 microns.

12. The system of claim 1, wherein each aperture has the same shape.

13. The system of claim 1 further comprising the fluid;
wherein the clustered particles are label-free.

14. The system of claim 1 further comprising the fluid;
wherein the clustered particles are labeled.

15. The system of claim 1, wherein the device has a diameter of between approximately 5 millimeters and approximately 300 millimeters.

16. The system of claim 1, wherein the device comprises a material selected from the group consisting of a fluorine-based polymer, a perfluoropolyether-based polymer, a heat-curable polymer, a UV-curable polymer, a metal, and a semiconductor.

17. A fabricating process for the isolation device of claim 1 comprising:
fabricating a silicon mold on a silicon wafer;
fabricating a polymer mold;
fabricating the isolation device; and
releasing the isolation device.

18. The fabricating process of claim 17, wherein fabricating the silicon mold on the silicon wafer comprises:
depositing a first photoresist layer on the silicon wafer;
patterning the first photoresist layer;
etching the silicon wafer to form a plurality of pillars;
depositing a nitride layer on the silicon wafer;
depositing a second photoresist layer;
patterning the second photoresist layer and the nitride layer;
etching the silicon wafer to form slanted sidewalls extending to each pillar of the plurality of pillars;
depositing a third photoresist layer;
patterning the third photoresist layer; and
etching the silicon wafer to form the silicon mold.

19. The fabricating process of claim 17, wherein fabricating the polymer mold comprises:
coating the silicon wafer with silane;
depositing a first polymer layer on the silicon wafer;
curing the first polymer layer to form a first polymer mold;
removing the first polymer mold from the silicon wafer;
coating the first polymer mold with silane;
depositing a second polymer layer on the first polymer mold; and
curing the second polymer layer to form the second polymer mold.

20. The fabricating process of claim 19, wherein the first polymer layer and the second polymer layer comprise polydimethylsiloxane (PDMS).

21. The fabricating process of claim 19 further comprising removing the second polymer mold from the first polymer mold.

22. The fabricating process of claim 19, wherein fabricating the isolation device comprises:
affixing the second polymer mold to a substrate;
filling the second polymer mold with a UV-curable polymer;
exposing the UV-curable polymer to UV light; and
curing the UV-curable polymer.

23. The fabricating process of claim 22, wherein a vacuum pump is used to fill the second polymer mold with the UV-curable polymer.

24. The fabricating process of claim 22, wherein the substrate is a vinyl dicing tape.

25. The fabricating process of claim 22, wherein the substrate is an acetate sheet.

26. The fabricating process of claim 22, wherein the substrate is a PET sheet.

27. The fabricating process of claim 22, wherein filling the second polymer mold with the UV-curable polymer is performed on a thermoelectric cooler.

28. The fabricating process of claim 22, wherein releasing the isolation device comprises:
removing the second polymer mold; and
removing the isolation device from the substrate.

29. A method for isolating clustered particles using the system of claim 1 comprising:
passing a fluid through the isolation device, the fluid comprising clustered particles and non-clustered particles;
capturing the clustered particles within the meshed trapping region; and
outputting the isolated fluid comprising the non-clustered particles.

30. The method of claim 29, wherein the fluid is blood, the non-clustered particles are cells, and the clustered particles are cell-clusters.

31. The method of claim 29, wherein the fluid is urine, the non-clustered particles comprise non-clustered cells, and the clustered particles comprise cell-clusters.

32. The method of claim 29 further comprising positioning the isolation device within a filtration holder.

33. The method of claim 29, wherein passing the fluid through the isolation device occurs at a flow rate of between approximately 20 mL/h and approximately 100 mL/h.

34. The method of claim 29 further comprising retrieving at least a portion of the clustered particles from the meshed trapping region.

35. The method of claim 34, wherein retrieving the clustered particles from the meshed trapping region comprises:
washing the clustered particles with PBS; and
transferring the clustered particles to a holding container.

36. The method of claim 34, wherein a micromanipulator retrieves the clustered particles directly from the meshed trapping region.

37. The method of claim 29 further comprising analyzing the clustered particles.

38. The method of claim 29 further comprising:

coating the isolation device with a growth culture, wherein the captured clustered particles grow on the coated isolation device; and analyzing the grown clustered particles directly on the coated isolation device.

39. The method of claim 29 further comprising coating the isolation device with a material selected from the group consisting of an inorganic material and an organic material.

40. A method of dissociating a clustered particle using the system of claim 1.

41. A system comprising:

an isolation device formed by a fabricating process and comprising:

an inlet;

microwells, each microwell including sidewalls and a bottom surface having a meshed trapping region; and an outlet;

wherein the device is configured to:

receive a fluid through the inlet comprising non-clustered particles and clustered particles; and output an isolated fluid through the outlet comprising at least substantially all of the non-clustered particles and being at least substantially free of the clustered particles;

wherein the meshed trapping region is configured to capture at least substantially all clustered particles of the fluid and pass at least substantially all non-clustered particles of the fluid; and wherein the meshed trapping region comprises at least four apertures configured to divide a flow of the fluid into at least four flow paths.

* * * * *